US009693882B2

(12) United States Patent
Lomeli et al.

(10) Patent No.: US 9,693,882 B2
(45) Date of Patent: Jul. 4, 2017

(54) OPTICAL TRIAL DEVICE

(71) Applicant: DePuy Synthes Products, Inc., Raynham, MA (US)

(72) Inventors: Roman Lomeli, Plymouth, MA (US); John Riley Hawkins, Cumberland, RI (US); Michael J. O'Neil, West Barnstable, MA (US); Kevin Yong Shin, Suwanee, GA (US); Mark Hall, Bridgewater, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 438 days.

(21) Appl. No.: 14/295,208

(22) Filed: Jun. 3, 2014

(65) Prior Publication Data

US 2015/0342757 A1    Dec. 3, 2015

(51) Int. Cl.
*A61F 2/46* (2006.01)
*A61B 19/00* (2006.01)

(52) U.S. Cl.
CPC ............ *A61F 2/4684* (2013.01); *A61B 19/46* (2013.01); *A61B 19/5212* (2013.01); *A61F 2/46* (2013.01); *A61B 2019/5217* (2013.01)

(58) Field of Classification Search
CPC .................................................. A61F 2/4684
See application file for complete search history.

(56) References Cited

U.S. PATENT DOCUMENTS

| | | | |
|---|---|---|---|
| 5,902,272 A | 5/1999 | Eggers et al. | |
| 6,113,639 A | 9/2000 | Ray et al. | |
| 6,440,141 B1 | 8/2002 | Philippon | |
| 6,695,839 B2 | 2/2004 | Sharkey et al. | |
| 6,723,097 B2 | 4/2004 | Fraser et al. | |
| 7,320,688 B2 | 1/2008 | Foley et al. | |
| 7,837,687 B2 | 11/2010 | Harp | |

(Continued)

FOREIGN PATENT DOCUMENTS

| | | |
|---|---|---|
| WO | 03/065949 A2 | 8/2003 |
| WO | 2006/033067 A2 | 3/2006 |

OTHER PUBLICATIONS

International Search Report and Written Opinion for Application No. PCT/US2015/032777, mailed Oct. 2, 2015 (10 pages).
[No Author Listed] SED Surgery. Desert Institute for Spine Care. Retrieved on Mar. 3, 2015 from <http://sciatica.com/sed-surgery>. Publication date is unknown. 17 pages.

(Continued)

*Primary Examiner* — Andrew Yang
(74) *Attorney, Agent, or Firm* — Nutter McClennen & Fish LLP

(57) ABSTRACT

An optical trial implant device that can be used to determine an appropriate size for an intervertebral disc implant can be configured so that one or more portions of the device can be optically transparent or radiolucent. The device can include an imaging device that can be used to view and image the intervertebral space through the optically transparent portion(s) of the device. The device can be used to determine the extent and quality of preparation of an intervertebral space between adjacent vertebral bodies for a surgical procedure, such as a disc replacement or spinal fusion procedure. The acquired image information can be transmitted to a mobile computing device for display in real time and/or stored for future use. The information may also be used to determine parameters indicating the quality of endplate surface preparation.

17 Claims, 11 Drawing Sheets

(56) References Cited

U.S. PATENT DOCUMENTS

| | | |
|---|---|---|
| 7,951,141 B2 | 5/2011 | Sharps et al. |
| 7,955,355 B2 | 6/2011 | Chin |
| 8,308,803 B2 | 11/2012 | Foley et al. |
| 8,343,035 B2 | 1/2013 | To |
| 8,394,142 B2 | 3/2013 | Bertagnoli et al. |
| 8,512,234 B2 | 8/2013 | Grey et al. |
| 2006/0069436 A1 | 3/2006 | Sutton et al. |
| 2006/0276694 A1 | 12/2006 | Acha Gandarias |
| 2008/0045897 A1 | 2/2008 | Collins et al. |
| 2008/0287959 A1 | 11/2008 | Quest et al. |
| 2009/0312805 A1 | 12/2009 | Lang et al. |
| 2010/0292801 A1 | 11/2010 | Hansell et al. |
| 2010/0331736 A1 | 12/2010 | Stein |
| 2011/0106259 A1 | 5/2011 | Lindenmann et al. |
| 2011/0213221 A1 | 9/2011 | Roche |
| 2013/0023990 A1 | 1/2013 | Zipnick et al. |
| 2013/0103153 A1 | 4/2013 | Blackwell et al. |
| 2013/0110238 A1 | 5/2013 | Lindemann et al. |
| 2015/0305878 A1* | 10/2015 | O'Neil ............... A61B 5/0084 623/17.16 |

OTHER PUBLICATIONS

[No Author Listed] YESS Selective Endoscopic Discectomy. Brochure. Desert Institute for Spine Care. 2006, 1 page.

Soehngen et al., Operation-microscope-mounted touch display tablet computer for intraoperative imaging visualization. World Neurosurg. Feb. 2012;77(2):381-3. doi: 10.1016/j.wneu.2011.06.017. Epub Nov. 7, 2011.

\* cited by examiner

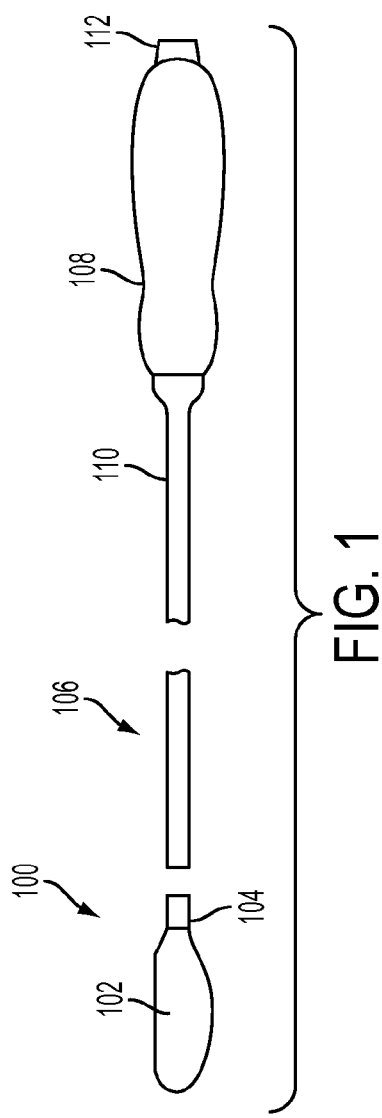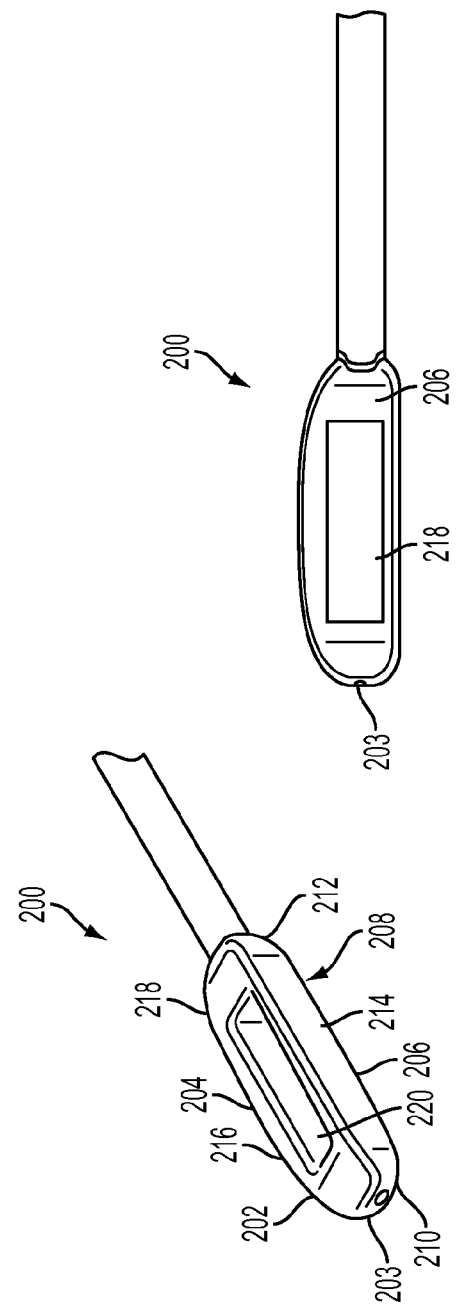

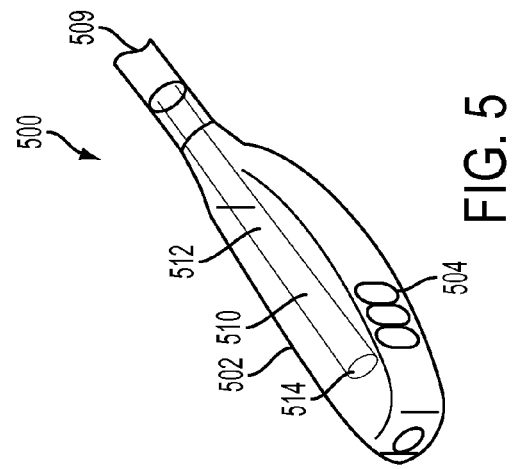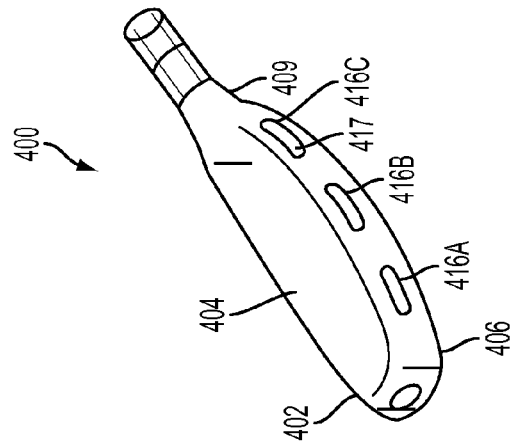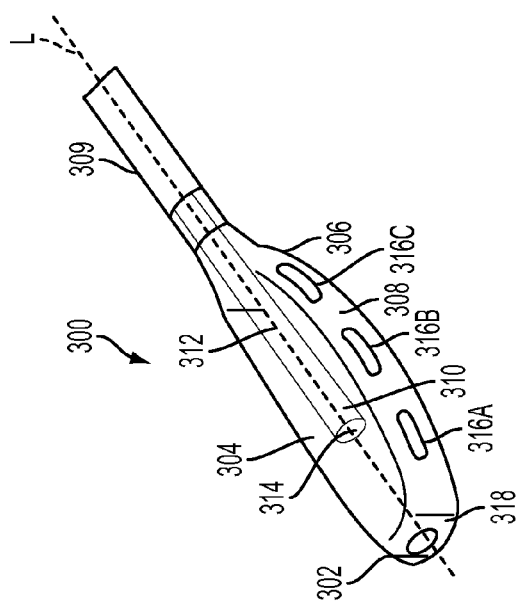

OPTICAL TRIAL DEVICE

FIELD

The present invention relates to using optical trial implant devices for verifying preparation of an endplate surface of a vertebral body for receipt of an intervertebral disc implant or a spinal fusion procedure.

BACKGROUND

Treatment for a diseased or damaged disc can involve the removal of the natural, damaged disc tissue, and the subsequent replacement of the disc with an implant, such as an interbody cage or fusion device, or a disc prosthesis. The implant should have an appropriate size and shape to complement the normal height of the disc and to contour the vertebral endplates adjacent the disc space to provide stability and, if a fusion device is being implanted, to promote fusion. If the shape of the vertebral endplates does not match the shape of the implant, shifting can occur resulting in misalignment of the vertebrae. Accordingly, it is important for the implant to correspond as closely as possible to the region of the intradiscal space that is receiving the implant.

Selection of a properly sized implant can be difficult due to the enclosed nature of the intervertebral disc space. X-rays generally reveal very little about the particular size and shape of the intradiscal space, and thus surgeons often have to rely on an estimated shape and size based on physiological factors, such as the patient's height, weight, etc., as well as the position of the vertebrae. While this method can be sufficient, the selection of an improperly sized implant can lead to problems. An oversized implant, for example, will be difficult to position between the adjacent vertebrae and can lead to long term problems once implanted. Moreover, due to the enclosed nature of the intervertebral disc space, it is virtually impossible for a surgeon to accurately evaluate the size and shape of the cavity, much less the matching of the implant with the vertebral endplates. Unfortunately, the sizing problem is not always discovered until the surgeon attempts to position the implant between the vertebrae. As a result, the implant will have been in direct contact with bodily fluids and will be contaminated and not recommended for reinsertion/implantations. Some implants can be virtually impossible to resterilize due to the nature of the materials from which they are made. In such cases, it is necessary to discard an expensive device.

To overcome this problem, trial implants and trial implant kits have been developed to assist surgeons in selecting an implant having the appropriate size and shape. U.S. Pat. No. 6,113,639 of Ray et al. discloses, for example, a trial implant kit containing several trial implants, each sized and shaped to simulate the size and shape of an available prosthetic implant. The surgeon can select an implant from the kit to temporarily position within the disc space to evaluate the size of the intradiscal space and the fit of a sample prosthesis. A contrast material can be injected into the nucleus cavity to view the trial implant with respect to the intradiscal space via a fluoroscope.

While fluoroscopy or x-ray can be effective to verify the placement of a trial implant, the image produced can be distorted by the large, opaque implant. This distortion can either shield or completely obscure the anatomical matching that the surgeon desires to verify. It can also be difficult to accurately assess whether the implant is in close contact with the complex geometries of the adjacent vertebral endplates.

Prior to implanting such an implant, it is also necessary to adequately prepare the surface of the vertebral endplates to ensure the best possible fit of the implant. This procedure typically entails removing the damaged disc and cleaning and shaping the endplate of each of the vertebrae. The sufficiency of the preparation of the endplate surface can influence the eventual fit of the implant and thus the outcome of the surgical procedure. However, existing techniques for assessing the endplate preparation to receive a desired implant are often insufficient to determine whether the endplate surfaces have been properly cleaned and the intervertebral space has been adequately prepared to accept the implant. In particular, it is difficult or impossible to view the disc space and the endplate surfaces. It is also challenging to accurately make free volume determinations or determine endplate contact area locations.

Accordingly, there remains a need for methods and devices for evaluating preparation of the surfaces of the adjacent vertebral bodies for accepting an implant and/or for performing a spinal fusion procedure.

SUMMARY

Some embodiments relate to an intervertebral trial device. In some embodiments, the intervertebral trial device can comprise a trial implant body configured to be placed between adjacent vertebral bodies, the trial implant body having an upper trial vertebral end plate surface configured to engage a first vertebral endplate, a lower trial vertebral endplate surface configured to engage a second vertebral endplate, and a perimeter wall connecting the upper and lower trial vertebral end plate surfaces. The perimeter wall can have a distal portion, a proximal portion, and opposed lateral portions. In the intervertebral trial device, at least one of the upper trial vertebral end plate surface, the lower trial vertebral end plate surface, and the perimeter wall can have at least a portion thereof that is optically transparent or translucent. The intervertebral trial device can further include an elongated handle extending from a portion of the perimeter wall.

The intervertebral trial device can have any number of variations. For example, the trial implant body can comprise an optically transparent or translucent material (e.g., polymer, glass, crystal, combinations thereof, and the like). For another example, the portion that is optically transparent can comprise an opening formed in at least one of the upper trial vertebral end plate surface and the lower trial vertebral end plate surface. For yet another example, the trial implant body can be removably and replaceably attached to the elongate handle. For another example, the intervertebral trial device can comprise at least one imaging device. For still another example, the elongated handle can include at least one optical element coupled with the at least one imaging device, the at least one optical element being configured to transmit signals from the at least one imaging device to a computing device. A proximal end of the elongated handle can be configured to be coupled with an attachment component configured to seat the computing device. For another example, the portion that is optically transparent can comprise at least one lens or prism. For another example, the at least one lens or prism can be removably disposed at least partially within the body. For yet another example, the portion that is optically transparent can comprise at least one opening formed in the perimeter wall. For another example, the at least one opening can be formed in the distal portion of the perimeter wall, in an anterior portion of the perimeter wall, and/or in a posterior portion of the perimeter wall. For another example, the at least one opening can be formed in the upper trial vertebral end plate surface and/or the lower trial vertebral end plate surface. For yet another example, the portion that is optically transparent can have at least one optical component for acquiring images of at least one of an intervertebral space between the adjacent vertebral bodies and at least one of the first and second vertebral endplates. For another example, the trial implant body can be expandable and/or inflatable.

In another embodiment, a method of verifying preparation of adjacent vertebral bodies for receiving an implant can comprise preparing an endplate surface of at least one of the adjacent vertebral bodies for a surgical procedure, positioning an optical trial device into an intervertebral space between the adjacent vertebral bodies, and verifying preparation of the endplate surface for receipt of an implant or a spinal fusion procedure by viewing portions of the intervertebral space and the endplate surface through the optical trial device positioned into the intervertebral space. Verifying preparation of the endplate surface can comprise acquiring at least one image of at least one of an intervertebral space between the adjacent vertebral bodies and the endplate surface. The optical trial device can comprise a trial implant body that is formed entirely of an optically transparent polymer or crystal. In some embodiments, the optical trial device can comprise an expandable trial device, and the method can further comprise inflating the expandable trial device when the expandable trial device is positioned in the intervertebral space.

Other embodiments can relate to an intervertebral trial kit. The intervertebral trial kit can comprise a plurality of optical trial devices, each configured to be placed in a prepared disc space between adjacent vertebral bodies. Each optical trial device of the plurality of optical trial devices can have an optical trial implant body configured to be placed between the adjacent vertebral bodies. The optical trial implant body can have an upper trial vertebral end plate surface configured to engage a first vertebral endplate, a lower trial vertebral endplate surface configured to engage a second vertebral endplate, and a perimeter wall connecting the upper and lower trial vertebral end plate surfaces. In some embodiments, the perimeter wall can have a distal portion, a proximal portion, and opposed lateral portions. In some embodiments, at least one of the upper trial vertebral end plate surface, the lower trial vertebral end plate surface, and the perimeter wall can have at least one portion thereof that is optically transparent.

The intervertebral trial kit can have any number of variations. For example, the intervertebral trial kit can further comprise an elongated handle configured to be removably attached to a portion of an optical trial device of the plurality of optical trial devices. For another example, the intervertebral trial kit can comprise an attachment component configured to seat a computing device that is configured to receive images of at least one of an intervertebral space between the adjacent vertebral bodies and at least one endplate of the adjacent vertebral bodies through the at least one portion that is optically transparent. In some embodiments, the computing device comprises a mobile computing device.

BRIEF DESCRIPTION OF THE DRAWINGS

The invention will be more fully understood from the following detailed description taken in conjunction with the accompanying drawings, in which:

FIG. 1 is a perspective, side view of an intervertebral trial device and a removable handle;

FIG. 2A is a perspective view of a portion of an exemplary intervertebral trial device;

FIG. 2B is a bottom view of the intervertebral trial device of FIG. 2A;

FIG. 3 is a perspective view of another exemplary intervertebral trial device;

FIG. 4 is a perspective view of another exemplary intervertebral trial device;

FIG. 5 is a perspective view of another exemplary intervertebral trial device;

DETAILED DESCRIPTION

Figure 6A:
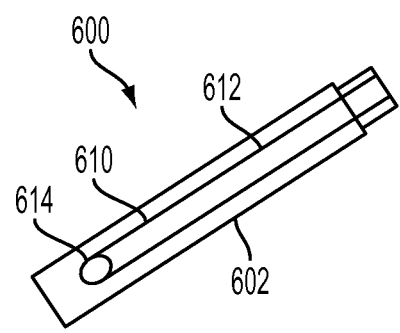
FIG. 6A is a perspective view of an expandable intervertebral trial device in a constrained configuration.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-numbered components of the various embodiments generally have similar features when those components are of a similar nature and/or serve a similar purpose.

Reference throughout the specification to "various embodiments," "some embodiments," "one embodiment," or "an embodiment," or the like, means that a particular feature, structure, or characteristic described in connection with the embodiment is included in at least one embodiment.

Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

Various spine surgical procedures, such as spinal fusion or disc replacement procedures require proper preparation of surfaces of adjacent vertebrae that are involved in the procedure. Furthermore, before an implant, such as an interbody cage or fusion device or a disc prosthesis can be inserted into an intervertebral space to replace a spinal intervertebral disc, the adjacent endplates are prepared to receive an implant, and a series of trial implant devices are placed in the intervertebral space to assess the size and fit of the implant. The trial implant devices can have different sizes and/or shapes and can be inserted, one by one, into the intervertebral space until an appropriately sized trial device is selected. Once such a trial device having an appropriate size is selected, the surgeon can implant into the intervertebral place the actual implant that corresponds to the selected trial device.

As previously mentioned, before the series of the trial implant devices are used to select an appropriately sized trial device or prior to the placement of an implant, the disc is completely or partially removed and the surfaces of the endplates of the adjacent vertebrae that are separated by the diseased or damaged disc are prepared to receive the implant. The vertebral surface preparation involves removing all or part of the damaged or diseased disc and cleaning the surfaces of the endplates. During the disc removal procedure, the intervertebral space often includes disc debris that can remain when the disc is not completely removed, as well as blood and other fluids. To determine whether the endplate surface has been adequately prepared, the surgeon typically relies on his or her tactile and sometimes aural senses. Specifically, the surgeon can use his or her finger, or an instrument such as a ball tip feeler, to determine, based on the surgeon's experience, whether the endplate surface feels like it has been prepared in a proper manner. Additionally, the surgeon can listen for specific sounds that are produced when the endplate surfaces are prepared using appropriate instruments (e.g., a curette, cob, or other disc removing instrument) and/or sounds that are generated when the endplate surfaces are contacted in any other manner. The manual examination and reliance on the surgeon's hearing may be insufficient and/or unreliable to determine whether the entire disc or its diseased portion has been completely removed and whether the endplate surfaces are sufficiently cleaned. Direct visual inspection of the endplate surfaces is only possible in certain procedures (e.g., some ALIF procedures), and use of visualization devices such as dental mirrors and the like is often inadequate. At the same time, a success of a spinal fusion or disc replacement procedure is largely dependent on the quality of preparation of the endplate surface.

The disclosure provides an improved approach to determine the quality of preparation of the endplate surface for receipt of an appropriate intervertebral implant. The approach may involve using trial implant devices that can be inserted into an intervertebral space between adjacent vertebrae to assess fit. However, the trial implant devices in accordance with some embodiments can include one or more optically transparent or radiolucent portions that allow direct visualization of the intervertebral space and the endplates. In particular, the optical trial device disclosed herein can include an optical element (e.g., one or more imaging devices and/or light sources) that allows the endplates to be viewed through the optically transparent portion(s) of the optical trial device.

In some embodiments, optical element(s), alternatively referred to herein as an imaging device or imaging elements, can be fixedly positioned with the optical trial device. In other embodiments, the imaging device can be coupled with an endoscope or other suitable device and can be passed to the body of the optical trial device through a proximal opening thereof. The field of view of the image device disposed within the trial device can be illuminated in any suitable manner. For example, in embodiments in which the imaging device is inserted within the trial device is coupled to a distal end of an endoscope, the distal end of the endoscope can also deliver light transmitted from a suitable light source, to illuminate the area being viewed. In embodiments in which the endoscope or similar device is not employed, the area viewed using the imaging device (e.g., a video camera) can be illuminated using one or more light emitting devices disposed within the body of the trial device.

Regardless of the way in which a light source delivers light to the area being viewed and imaged, one or more light sources used in connection with the described optical trial devices can be configured to deliver light beams having multiple, different wavelengths. In some cases, one or more of visible, ultraviolet, and infrared light can be utilized to image the intervertebral space. A light source can be equipped with a filter to select between different wavelengths, or it can be otherwise controlled to illuminate the intervertebral space.

The techniques in accordance with some embodiments may allow visualizing the intervertebral space and endplate surfaces in a minimally invasive way because an optical trial device that is already used to determine an appropriate implant size, shape and position is additionally utilized to view the area prepared for accepting the implant. The use of the imaging device rather than reliance on a tactile and audible examination by a surgeon or other medical professional permits acquiring more reliable information about the intervertebral space into which an implant is to be inserted. Furthermore, if known techniques involving the use of an endoscope coupled with an imaging device are utilized to view an intervertebral space, damaged disc material, blood and other fluids can obstruct the surgeon's field of view. The described optical trial device allows obtaining images of an improved quality because the device can be pressed against the surface to be imaged and thus can push the disc remains, blood and other fluids away from that surface, thereby clearing the field of view. Thus, the material that may typically impede the examination of the endplate surfaces no longer obscures the surfaces that are being viewed and evaluated.

Furthermore, pressing the trial device against the surface of an endplate allows identification of areas of the endplates that are contacted by the optical trial device and areas that are not contacted. This can allow a determination of the extent and quality of preparation of the endplate surfaces for the surgical procedure. Contact area can be an important indicator of the likelihood of subsidence.

As discussed above, the described optical trial device that allows viewing the intervertebral space and endplate surfaces can have one or more portions that are optically transparent. In some embodiments, the entire surface of the trial device can be optically transparent, which can allow visibility around the entire surface of the device. In some embodiments, the trial device can be positioned in the intervertebral space between two adjacent vertebrae after the disc has been removed and, the optical trial device can remain in the same position as it is used to view and image the intervertebral space and endplate surfaces.

In some embodiments, the trial device can be coupled to an assembly comprising a mobile computing device, such as a smartphone or any other mobile computing device as known in the art or developed in the future. In such embodiments, a camera of the mobile computing device can be conveniently used to record and display the image information acquired through the trial device. The image information can be displayed on a screen of the computing device in real time during the surgery. Additionally, the image information can be stored in a suitable storage media (e.g., an external database) for future use.

Regardless of the type of the trial device configured in accordance with some embodiments, image information acquired by an imaging element through the trial device can be transmitted to a suitable computing device that can display the information and process it in any suitable manner. For example, as discussed above, the image information can be used to identify one or more endplate surface areas that are contacted by a trial device and one or more areas that are not in contact with the trial device when the device is pressed against the endplate surface and used to image that surface. Furthermore, various qualitative and quantities parameters describing the extent and quality of the endplate surface preparation can be determined and presented on a display of a suitable computing device. In embodiments where the disc replacement procedure is performed, viewing the intervertebral space through the trial device can further be used to determine how well the trial device fits into the intervertebral space to thereby determine an appropriately sized trial device with an improved precision.

FIG. 1 illustrates an embodiment of an intervertebral trial device 100, which is sometimes referred to herein as an optical trial device. As shown, the optical trial device 100 includes a body 102 that is configured to be placed between adjacent vertebral bodies of a patient's spinal column and an adapter 104 that can be used to connect the optical trial device 100 to a handle 106 or other introducer instrument. In some embodiments, as shown in FIG. 1, the handle 106 can comprise a base 108 configured to be held by a surgeon and an elongate shaft 110. The shaft 110 can have any suitable length and can be formed of any suitable material, including metals and polymers. It should be appreciated that embodiments are not limited to a handle of any specific shape, size, or a way in which the handle can mate with the optical trial device 100, and any instrument that can be used to hold the optical trial device 100 can be employed. In some embodiments, the handle 106 can be a conventional or modified endoscope that is configured to insert the trial device in the intervertebral space.

The optical trial device as described herein can be any suitable trial device having any suitable size and shape. In some embodiments, the trial device may have a size and shape so as to fit in the intervertebral space and thereby be used to determine an appropriate size for an artificial intervertebral disc intended to replace the natural disc. For example, the trial device can have a rectangular, oblong, rounded or other shape. Furthermore, the optical trial device can be formed of a rigid or flexible material or any combination thereof. In some embodiments, the optical trial device can have various features conforming to the shape of the intervertebral space, features useful for inserting the optical trial device between adjacent vertebral bodies, and any other features.

FIGS. 2A and 2B show an exemplary optical trial device 200 that can include a trial implant body 202 comprising an upper trial vertebral end plate surface 204 configured to engage a first vertebral endplate, and a lower trial vertebral endplate surface 206 configured to engage an adjacent, second vertebral endplate. The trial implant body 202 can also comprise a perimeter wall 208 connecting the upper vertebral end plate surface 204 and the lower trial vertebral end plate surface 206. The perimeter wall 208 can have a distal portion 210, a proximal portion 212, and opposed lateral portions 214 and 216.

In FIGS. 2A and 2B, the optical trial device 200 has a tapered distal end 203 having a bullet-like or generally trapezoidal shape in which a distal most end thereof is tapered to facilitate entry into an intervertebral space. It should be appreciated, however, that the distal end having such shape is shown by way of example only, as embodiments are not limited to any specific configuration of the distal end or other portions of the optical trial device.

The optical trial device 200 can include one or more optically transparent or radiolucent portions which enhance viewing portions of the intervertebral space and the endplate surface when the device is positioned within the intervertebral space.

The one or more optically transparent portions in the optical trial device 200 shown in FIGS. 2A and 2B or any other trial device in accordance with the embodiments described herein can be located in at least one of upper trial vertebral end plate surface, the lower trial vertebral end plate surface, and the perimeter wall of the trial device. In some embodiments, the entire surface of the trial device can be transparent. Further, one or more imaging elements can be positioned within the body of the optical trial device 200 to facilitate viewing of the intervertebral space through the trial device. By way of example, the imaging elements can be passed through the optical trial device via an optical conduit that can extend into the optical trial device from another device, such as, for example, an endoscope or other suitable device having its distal portion partially inserted into the optical trial device 200. In some embodiments, one or more imaging elements can be coupled (removably or fixedly) to the optical trial device, and no additional device such as an endoscope may be required. The imaging elements can comprise charge-coupled device (CCD) image sensors, complementary metal-oxide-semiconductor (CMOS) image sensors, or any other types of image sensors. It should be appreciated that the optical trial devices described herein can be used to visualize the intervertebral space using any suitable type of imaging devices, as embodiments are not limited in this respect.

In the embodiment illustrated in FIGS. 2A and 2B, the optical trial device 200 can have the optically transparent portion that comprises an opening 218 formed in each of the upper trial vertebral end plate surface 204 and the lower trial vertebral end plate surface 206. It should be appreciated that, in some embodiments, the opening can be formed in one of the upper trial vertebral end plate surface 204 and the lower trial vertebral end plate surface 206.

Although FIGS. 2A and 2B illustrate the opening 218 to be generally rectangular cross-section, the optically transparent openings can have any suitable shape.

In some embodiments, the opening 218 can comprise an optical component 220, such as, for example, an optical lens, prism, combined lens and prism or any other optical component. The optical component 220 may have any suitable optical characteristics. Moreover, the optical component 220 can be integrally coupled with the body 202 of the trial device 200 (e.g., integrally formed), or it can be removable. In embodiments in which the optical component 220 is removable, it may be disposable. Alternatively, the optical component can be reusable, in which case the optical component is formed of a material that allows proper sterilization of the component.

FIG. 3 illustrates another example of an optical trial device 300 comprising a body 302 having an upper trial vertebral end plate surface 304, lower trial vertebral end plate surface 306, and a perimeter wall 308. In this device, the entire upper trial vertebral end plate surface 304 can be optically transparent. As shown in FIG. 3, an imaging device 314 can be disposed within the body 302 for use in visualizing a surgical site in accordance with the present disclosure. The imaging device 314 can be coupled to a distal end 310 of a shaft 312 of a handle 309, which can be used to manipulate the imaging device 314 with respect to the body 302. More particularly, the shaft 312 can be inserted into the trial device 300 through a hollow channel of the handle 309 coupled with the trial device, a portion of which is shown in FIG. 3. In some embodiments, the handle 309 may be part of an endoscope or other instrument configured to insert the optical trial device into the intervertebral space and deliver an imaging device into the body of the optical trial device. It should be appreciated that any suitable type of endoscope or other device can be used to deliver the imaging device 314 inside the body 302 and thus embodiments are not limited in this respect.

The shaft 312 can be movable axially along a longitudinal axis L extending therethrough such that the imaging device 312 coupled to the distal end 310 of the shaft 312 can be moved to different axial positions within the body 302. In this way, images of different portions of the intervertebral space, including portions lateral to the body of the trial device, can be obtained through the trial device. This, in turn, can allow the intervertebral space being treated to be more easily assessed and prepared to receive an implant. In other embodiments, the component delivering the imaging device 314 can be configured to be stationary within the body 302. In still further embodiments, the imaging device 314 can be freely positioned with respect to the body 302 and no additional insertion instruments can be associated therewith.

The intervertebral space can be viewed in real time as a surgeon inspects the vertebral surface within the field of view of the imaging device in preparation for a spinal procedure. Thus, the progress of the endplate preparation procedure can be monitored by viewing images acquired by the imaging device and displayed on a suitable display. Further, the images can also be stored in a memory of a computing device for later use. For example, images may be later assessed by other medical professionals, evaluated for compliance purposes, used to determine what may have caused any complications if they occur, or used for any other suitable purposes.

Another advantage of the described approach is that the intervertebral space can be evaluated in an improved, minimally invasive manner, because the imaging device is incorporated within the optical trial device that is already used to assess the surgical site. No additional disturbance may be caused to the surgical site because no separate imaging device is used. Moreover, a manual assessment by a surgeon may not be required or can be limited when the described optical trial device is utilized.

As also shown in FIG. 3, the trial device 300 can additionally include optically transparent openings 316A-316C disposed in the perimeter wall 308. Similar openings can be located on the opposite side of the wall 308 not seen in FIG. 3. In the illustrated embodiment, there are three openings each having an elliptical or rounded shape, although any number and shape(s) of openings can be used without departing from the spirit of the present disclosure. In some embodiments, the openings in the same trial device may have different shapes and sizes.

The imaging device 314 can be positioned in the trial device 300 such that the intervertebral space is visible through one or more of the openings 316A-316C and/or the upper trial surface 304. It should be appreciated that the endoscope having the imaging device 314 at its distal end 310 can also deliver light to the field of view of the imaging device 314, using any suitable techniques known to the skilled in the art. Additionally or alternatively, in some embodiments, one or more light emitting devices, such as, for example, one or more light-emitting diodes (LEDs) or any other suitable types of light emitting devices, can be positioned within the body 302 of the trial device 300 to provide light to the field of view.

FIG. 4 illustrates another optical trial device 400 that can be inserted into an intervertebral space. The optical trial device 400 can include a body 402 having an upper trial vertebral end plate surface 404, a lower trial vertebral end plate surface 406, and a perimeter wall 408. In this exemplary device, the upper trial vertebral end plate surface 404 is not transparent, but one or both sides of the perimeter wall 408 can include openings 416A, 416B and 416C through which the intervertebral space can be visualized. In some embodiments, one or more of the openings 416A-416C can have an opaque shield that can be used to open and close the openings. Accordingly, as shown in FIG. 4, the opening 416C can be closed by a shield 417. It should be appreciated that any of the openings formed in a body of trial devices described herein can include a shield or other mechanisms that allow the openings to be opened and closed. Furthermore, in some cases, each opening can be associated with a shield. Additionally or alternatively, a shield can be configured to more than one opening. The shields can be operated manually (e.g., before the trial device is inserted into the patient's body), or in any other manner. In some embodiments, one or more actuators can be employed to control opening and closing of one or more shields.

In some embodiments, a substantial portion or even all of the surface of a trial device can be formed of an optically transparent material. FIG. 5 illustrates an optical trial device 500 having a body 502 that is entirely transparent. For example, the body 502 can be formed entirely of an optically transparent material, such as a polymer or any other material. Similar to the trial device 300, the trial device 500 can have inserted therein a shaft 512 of an endoscope 509 or other instrument having an imaging device 514 positioned on a distal end 510 thereof. In some embodiments, the shaft 512 can also deliver light to the imaging area, which can be provided from an external light source via an optical conduit such as an optical fiber or other type of conduit. Additionally or alternatively, in some embodiments, as shown by way of example in FIG. 5, the trial device 500 can include one or more light emitting devices 504. The light emitting devices 504 can comprise, for example, LEDs or any other suitable types of light emitting devices. For example, the light emitting devices can additionally or alternatively comprise one or more laser diode (LDs), or any other light sources, as embodiments are not limited in this respect. Furthermore, even though three light emitting devices 504 are shown in FIG. 5, it should be appreciated that the optical trial device described herein can include any number of light emitting devices of any suitable type.

An optical trial device described herein can be manufactured from any suitable material. In some embodiments, the optical trial device can be formed from an optically transparent polymer and can be rigid. In some embodiments, the trial device can be an expandable device that can be inserted into an intervertebral space in a constrained configuration. Once positioned in the intervertebral space, such trial device can be expanded, or inflated in a suitable manner to conform to the shape of the intervertebral space. The expandable optical trial device can be formed from any suitable material.

In some embodiments, one or more optically transparent portions of the trial device, such as openings 218, 316A-316C and 416A-416C, and, in some instances, an upper trial vertebral end plate and/or a lower trial vertebral end plate, can be formed of any suitable materials. In some embodiments, the optically transparent portions can be formed of an optically transparent or translucent material (e.g., polymers, glasses, etc.). Exemplary optically transparent or translucent materials include, for example, polycarbonate, acrylic polymer, plasticized polyvinyl chloride, polystyrene, polymethyl methacrylate, polyethylene terephthalate (PET), polyethylene terephthalate glycol-modified (PET-G) polymer, polysulfones including polyphenylsulfone (PPSU), polypropylenes, nylons (polyamides), acrylonitrile-butadiene-styrene (ABS), glass, tempered glass, optics grade glass, allyl diglycol carbonate (CR-39), NXT™ urethane polymers, crystals, and any other suitable materials.

Figure 6B:
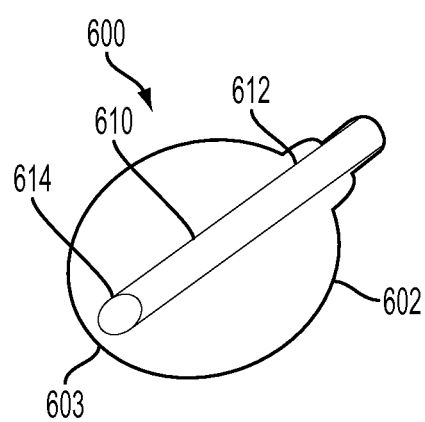
FIG. 6B is a perspective view of the expandable intervertebral trial device of FIG. 6A in an expanded configuration.

In some embodiments, the optical trial device can be expandable. FIGS. 6A and 6B illustrate an expandable optical trial device sometimes referred to herein as a balloon trial device. The trial device 600 can include an expandable body 602 configured to move from a constrained configuration, as shown in FIG. 6A, to an expanded configuration shown in FIG. 6B. In some embodiments, the entire body of the trial device 600 can be optically transparent. As a result, an imaging device 614 disposed on a distal end 612 of a shaft 612 of an endoscope or other instrument disposed in the body 602 can be used to visualize the surgical site. When the entire body of trial device is transparent, visualization through the transparent portion can be guided using built in prismatic features.

The optical trial device 600 can be inserted into the intervertebral space in the constrained configuration and then expanded—e.g., inflated with a clear fluid or gas. While many techniques known to those skilled in the art can be used to expand the trial device 600, in the illustrated embodiment, the trial device 600 can be expanded into a balloon configuration or other type of configuration. In some embodiments, when expanded, the trial device 600 can conform to the shape of the intervertebral space. In the expanded configuration, the trial device 600 can be pressed against the surfaces of the vertebral body endplates such that the device 600 pushes blood or other fluids in the intervertebral space away from the surface being imaged. In this way, the imaging device 614 can be used to obtain images of the endplates and the surrounding disc space with an improved quality.

It should be appreciated that even though the imaging device 614 in FIGS. 6A and 6B is shown as being inserted into the trial device 600 using the shaft 612, in some embodiments, the imaging device 614 can be embedded within the body 602 of the trial device 600. One advantage of using an expandable optical trial device like device 600 is that it can be soft and thus may not cause any significant disturbance to the surgical site. In addition, because the expandable optical trial device can conform to the topology of the intervertebral space, it can allow voids in the disc space that may be otherwise difficult to reach to be more easily viewed.

Figure 7:
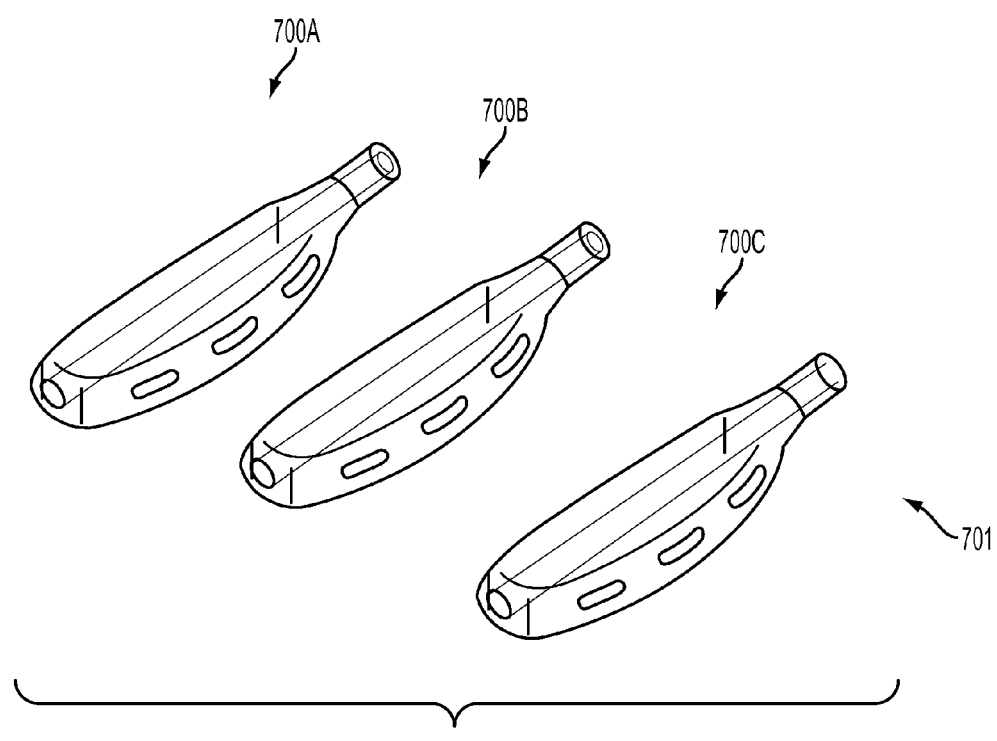
FIG. 7 is a perspective view of an exemplary kit having a plurality of intervertebral trial devices.

In some embodiments, an optical trial device kit may be provided for use in a surgical procedure. The kit can include a plurality of optical trial devices, each configured to be placed in a prepared disc space between adjacent vertebral bodies. FIG. 7 illustrates an exemplary kit 701 including optical trial devices 700A, 700B and 700C, with the trial devices 700A, 700B and 700C being progressively greater in size. When using the kit, the surgeon can, for example, insert the smallest trial device 700A in the prepared intervertebral space first. If it is determined that the trial device 700A is smaller than a desired prosthetic intervertebral disc, the larger trial device 700B can be utilized. In the similar fashion, if the trial device 700B still does not have the appropriate size, the trial device 700C can be used next. However, the trial device kit 701 is shown by way of example only. In embodiments where a spinal fusion procedure is performed, trial devices of different sizes may be used to determine which device is more suited to view and image the intervertebral space.

In the example of FIG. 7, each of the optical trial devices 700A-700C can be configured in a manner similar to the trial devices 300, 400 or 500. However, it should be appreciated that the devices included in the kit can have a wide variety of shapes and sizes. The trial devices in a kit can be sized and shaped to simulate the size and shape of a natural disc that is being removed. In embodiments where the intervertebral space is evaluated prior to the disc replacement procedure, the trial devices in a kit can be sized and shaped to simulate the size and shape of a corresponding artificial intervertebral disc implant. Further, a person of skill in the art will recognize that a variety of other tools and devices useful in a spinal vertebral implant procedure can also be included as part of the kit.

Figure 8:
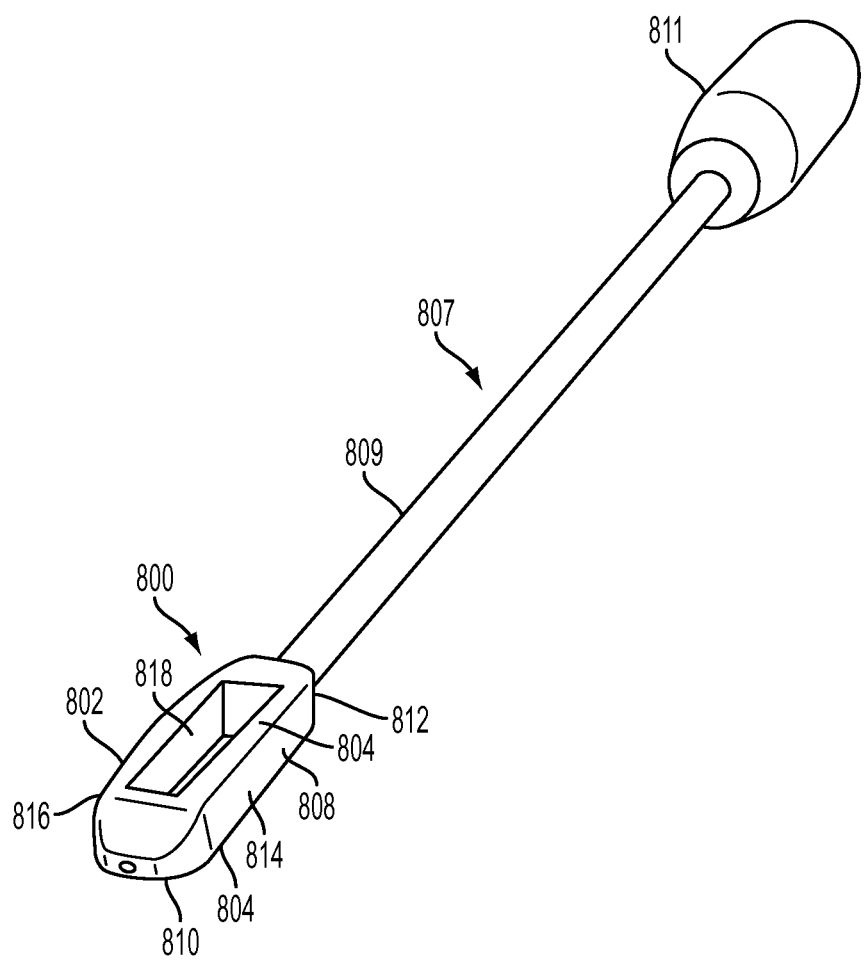
FIG. 8 is a perspective view of an exemplary intervertebral trial device.

FIG. 8 shows another exemplary optical trial device 800 having a trial implant body 802 having an upper trial vertebral end plate surface 804 configured to engage a first vertebral endplate, a lower trial vertebral endplate surface 806 configured to engage an adjacent, second vertebral endplate, a perimeter wall 808 connecting the upper vertebral end plate surface 804 and the lower trial vertebral end plate surface 806. The perimeter wall 808 can have a distal portion 810, a proximal portion 812, and opposed lateral portions 814 and 816. The perimeter wall 808 can have an opening 818 can be formed in each of the upper trial vertebral end plate surface 804 and the lower trial vertebral endplate surface 806, and can be configured to be optically transparent to permit visualization by an imaging device (not shown) disposed within the body 802.

As shown in FIG. 8, the proximal portion 812 can be coupled with an elongated handle 807 which can include a shaft 809 and a base 811. The base 811 can be configured to conveniently fit within the surgeon's hand. It should be appreciated that the shaft 809 and base 811 can have any suitable size and shape.

In some embodiments, the optical trial device 800 can be configured such that different trial devices or "heads" can be interchangeably used with the same handle. For example, different heads can fit on the shaft 809. In some embodiments, one or more optical trial devices can be disposable while the handle 807 can be reusable. In other embodiments, the trial device 800 can be reusable and can be sterilized after each use.

Figure 9:
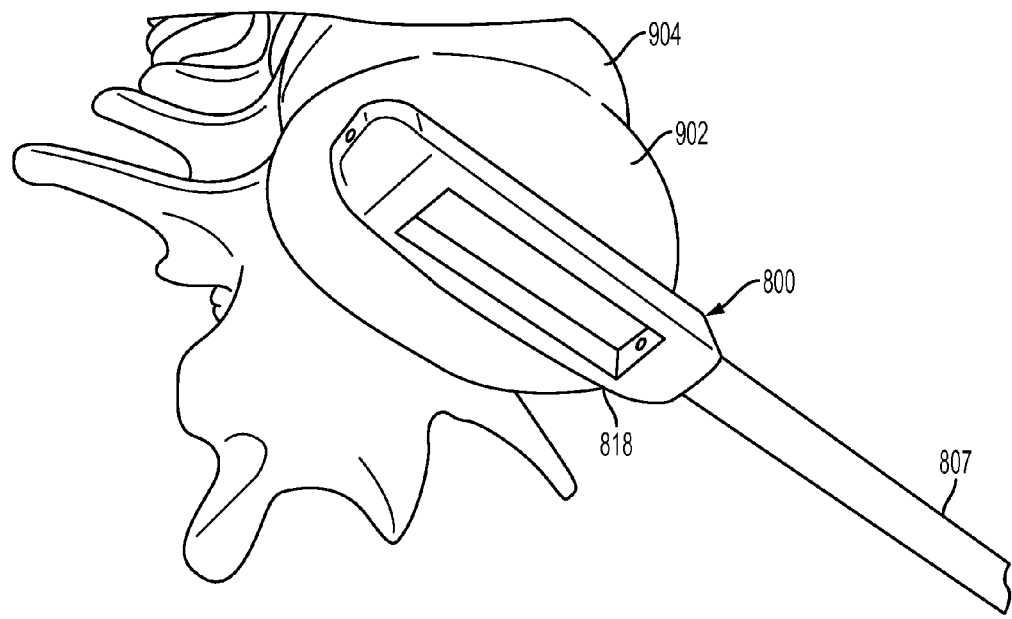
FIG. 9 illustrates an endplate of a vertebra with the intervertebral trial device of FIG. 8 positioned over the endplate.

FIG. 9 illustrates the device 800 in use, providing a posterior view of an endplate 902 of a vertebra 904 with the device 800 positioned over the endplate 902. An adjacent vertebra is not shown for the sake of simplicity. The opening 818 in the body 802 of the trial device 800 can be used to view the surface of the endplate 902 in accordance with some embodiments. It should be appreciated that the way in which the optical trial device 800 is positioned over the endplate 902 in FIG. 9 is shown by way of example only, and the device 800 can be inserted into the intervertebral space in a variety of ways.

Figure 10:
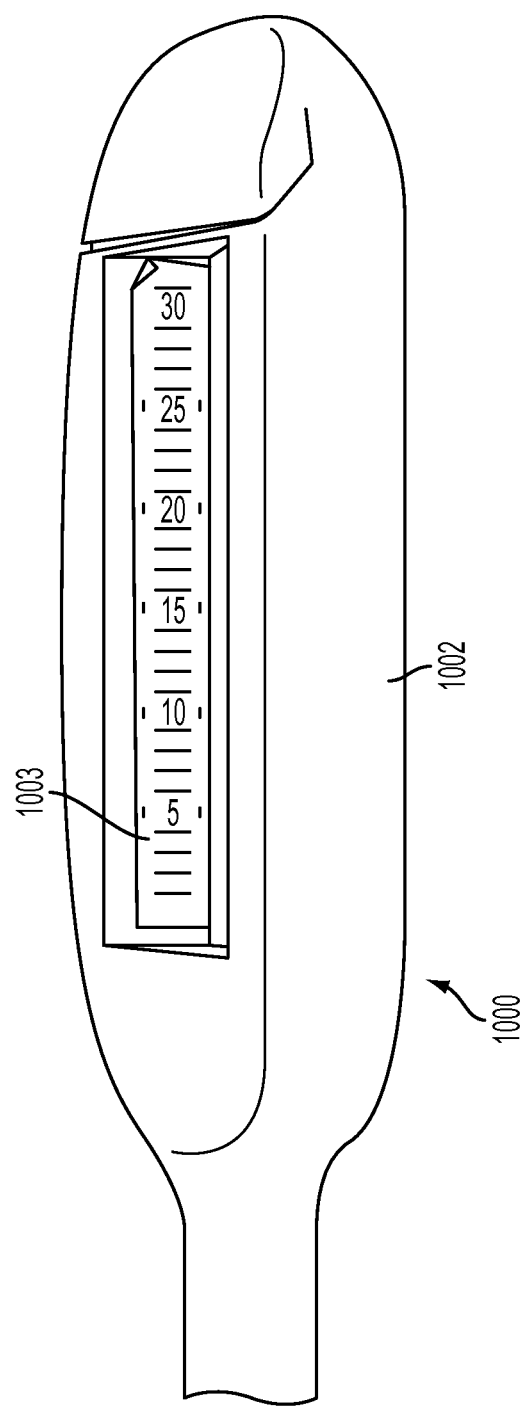
FIG. 10 is a perspective view of an intervertebral trial device including markings.

In some embodiments, an optical trial device as described herein can include other features that can be useful to a surgical procedure. By way of a non-limiting example, in some embodiments, components configured to determine the depth of insertion of the optical trial device and any other suitable parameters (e.g., position and alignment of the trial device with respect to the endplates) can be incorporated into the optical trial device. The components can include, for example, markers associated with any of the body of the optical trial device, the imaging device or a portion of the device that delivers the imaging device into the optical trial device body. FIG. 10 illustrates one exemplary optical trial device 1000 that has markings 1004 associated with a body 1002 thereof. The markings can have any suitable size and shape. In the illustrated embodiment, the markings 1004 include multiple measurement lines to designate a distance. However, it should be appreciated that any other type of markings or indicia can be used, as embodiments are not limited in this respect. Additionally or alternatively, in some embodiments, the optical trial device can be associated with one or more instruments such as a potentiometer, a linear position sensor or any other device that can be used to determine the depth of insertion of the optical trial device and/or a position and alignment of the optical trial device with respect to the endplates. The optical trial device can also include one or more optical markers to facilitate use with surgical navigation devices (e.g., navigation devices available from Brainlab AG).

Figure 11:
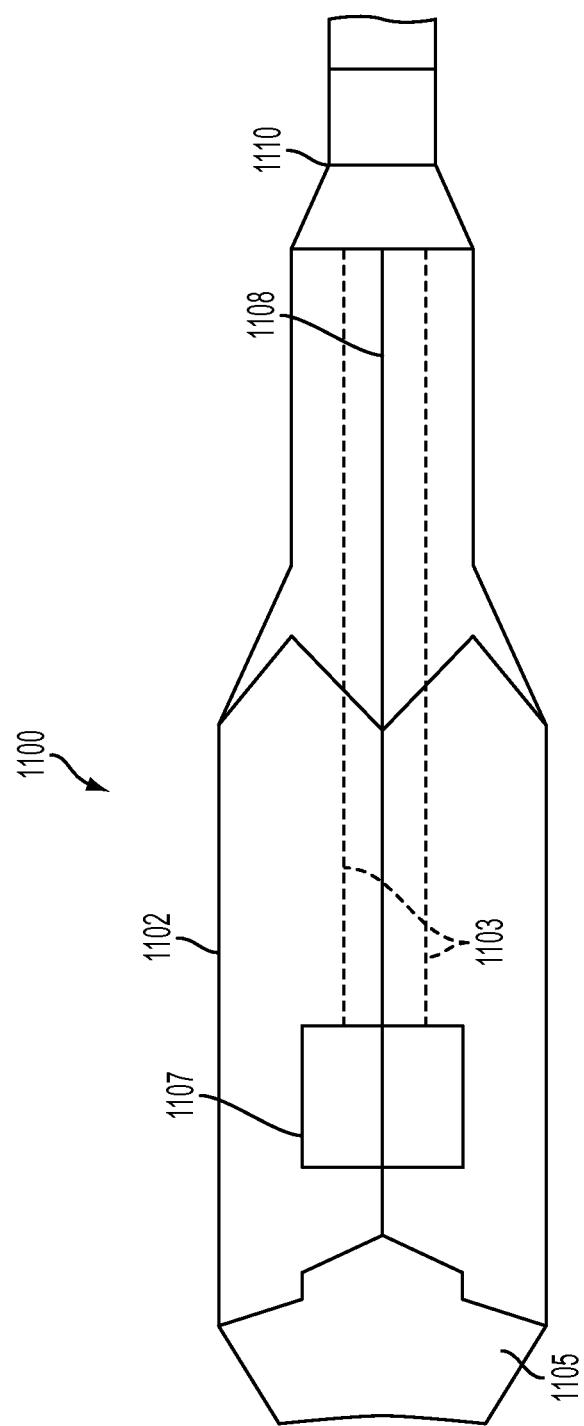
FIG. 11 is a perspective view of an intervertebral trial device having an optically transparent body in accordance with some embodiments.

FIG. 11 illustrates an exemplary optical trial device 1100 having a body 1102 that is optically transparent. At least a portion of the body 1102 can be configured as a prism, lens or a combination of a prism and lens having any suitable cross-sections. As shown, portions of the body 1102 can include hollow tube prisms 1103 each having a face that can be angled to provide viewing at different angles. For example, one of the prisms 1103 can be used to view a superior endplate surface, while another prism can be used to view an inferior endplate surface. In some embodiments, the optical trial device 1100 can remain at a single location while the intervertebral space can be viewed under different angles. Accordingly, an angled or side viewing of the intervertebral space may be achieved and, in some cases, the entirety of the endplate surface(s) can be viewed and imaged. Thus, the optical trial device 1100 can be used to view the intervertebral space from superior, inferior, and lateral positions with respect to the trial device. Further, it should be appreciated that the device 1100 and prisms 1103 can have any suitable geometry and can be made of any suitable material, including at least some portions of the device 1100 and/or prisms 1103 being made of an optically transparent material.

As shown in FIG. 11, the optical trial device 1100 can include a light source 1105 such as, for example, one or more LEDs and/or LDs. However, any other types of light sources can be utilized. The device 1100 can also include an imaging device 1107 (e.g., a video camera) that can be inserted into the device 1100 via a suitable conduit 1108 or can be otherwise coupled with the device 1100.

It should be appreciated that optical trial devices in accordance with some embodiments, including the device 1100, can include any other components that are not shown for the sake of simplicity. For example, the light source 1105 can be battery operated and a battery can therefore be positioned within the trial device 1100. Furthermore, the device 1100 can include a microcontroller and/or other processing device that can be configured to control operation of the light source 1105 and/or the imaging device 1107. The microcontroller can communicate (e.g., wirelessly) with an external computing device to receive instructions from the computing device and/or to transmit information acquired by the imaging device 1107 to the computing device. The information may comprise a single image or a sequence of images (e.g., a video), and can be displayed by the computing device on any suitable display. In some embodiments, the imaging device 1107 can be a wireless camera, and the optical trial device can include a wireless transmitter and receiver and/or any other components for wireless communication between the imaging device 1107 and the computing device. In some embodiments, the imaging device can be configured to capture spectral images or to perform spectral imaging techniques.

A proximal portion 1110 of the trial device 1100 can be configured to mate directly or indirectly with an attachment for a mobile computing device configured to receive image data acquired by the imaging device 1107. The mobile computing device can display the image data that can be viewed by the surgeon and/or other medical personnel in real time. Additionally, in some embodiments, the mobile computing device may process the image data, as discussed in more detail below. In some embodiments, image data acquired by the imaging device can be communicated via a wired or wireless connection to an electronic display monitor disposed in the operating room where the image data can be displayed.

It should be appreciated that, in some embodiments, the trial device 1100 can include an optical component such as a prism or lens, or a combination of a prism and lens formed only on a portion of the device. For example, a distal end of the body of the trial device can have a built-in optical component while other portions of the body of the device can be formed in other manner.

Figure 12:
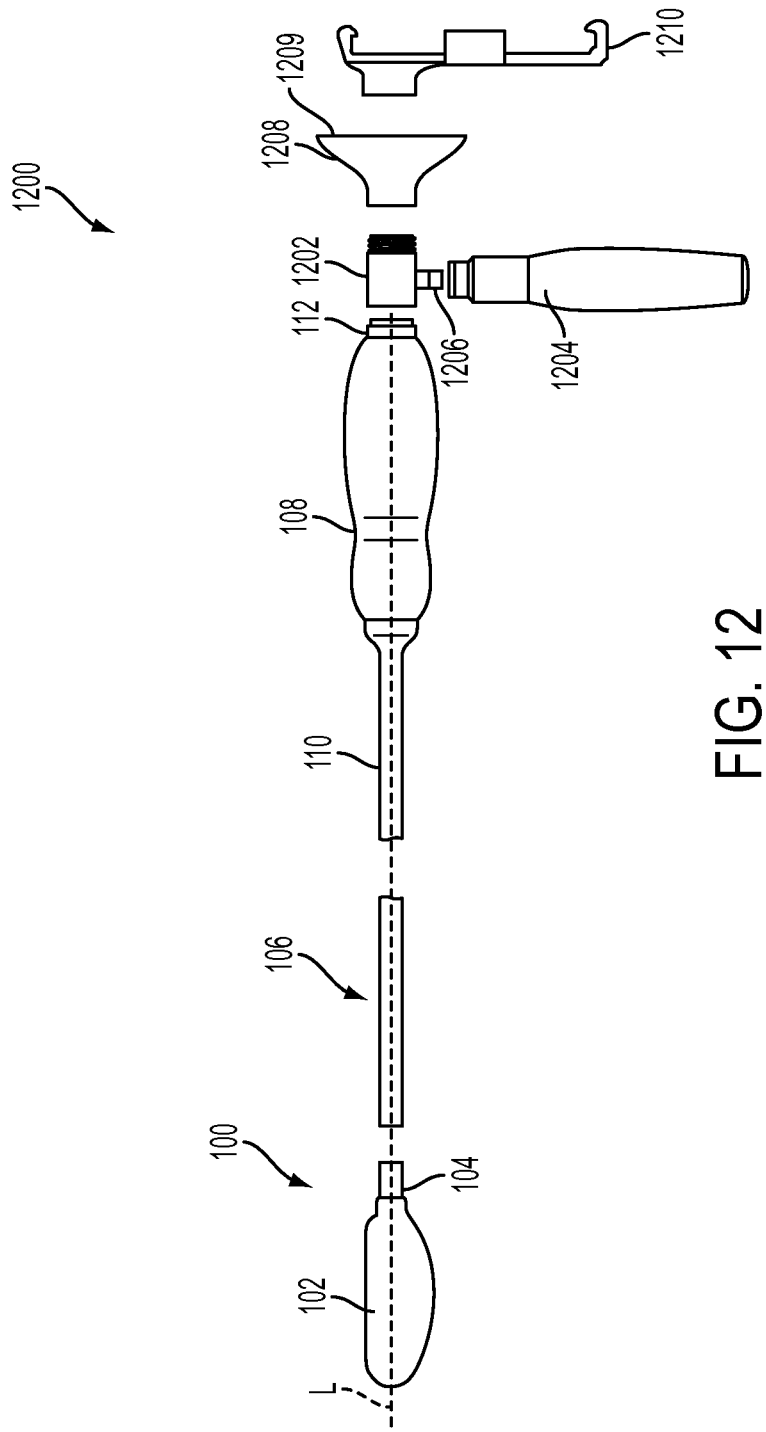
FIG. 12 is a perspective, side view of the intervertebral trial device of FIG. 1 and an imaging assembly in accordance with some embodiments.

The imaging device can be positioned by using an instrument (e.g., a rigid or flexible endoscope) that is configured to insert the imaging device inside the body of the optical trial device. FIG. 12 illustrates one instance in which the trial device 100 as shown in FIG. 1 is coupled with an imaging assembly 1200. As shown, the imaging assembly 1200 can include a light adapter 1202 coupled with a light source 1204 via an attachment 1206. The light source 1204 can be a battery powered light source or other type of light source. Light from the light source 1204 can be delivered to the imaging device (not shown) disposed in the body 102 using any suitable optical conduit. For example, an optical fiber system can be utilized. The imaging assembly 1200 can further include an eye piece attachment 1208 for observing the image transmitted from the imaging device and a mobile device attachment 1210 configured to seat a suitable computing device, such as a mobile telephone.

In use, the optical trial device 100 can be inserted into an intervertebral space between two adjacent vertebral bodies. As discussed throughout this disclosure, the device can configured so that an imaging device associated therewith can be used to view and image one or both of the endplates of the adjacent vertebral bodies and the surrounding intervertebral space. As a result, a quality of the preparation of the endplate surfaces and intervertebral space for receipt of an intervertebral disc implant can be evaluated.

The mobile device attachment 1210 can be configured to mount a mobile computing device such as, for example, a smartphone, a tablet or any other suitable computing device. It should be appreciated that the mobile device attachment 1210 can have any suitable configuration, and thus the configuration illustrated and described herein does not limit the configurations of attachments that can be used in conjunction with the present disclosure. The mobile device attachment 1210 can be configured such that, when it is used to seat a mobile computing device, a camera of the mobile computing device is aligned with an aperture 1209 of the eye piece attachment 1208.

In some embodiments, the handle 106 that is used to insert the trial device 100 in the intervertebral space can be an inserter instrument, such as an endoscope, configured for this purpose. The endoscope can be adjustable such that it can rotate about a longitudinal axis L extending therethrough. Accordingly, the imaging device positioned on a distal end of the endoscope (e.g., the imaging device 314 shown in FIG. 3 or any other imaging device) can be rotated to view the surrounding intervertebral space from a superior, inferior, and/or lateral position. The trial device 100 may remain in the same position as the imaging device is rotated.

The optical trial devices in accordance with some embodiments can be inserted into the intervertebral space using a variety of techniques. In some embodiments, the position of the trial device can be adjusted using instruments known in the art, such as cams, jacks, pistons, and any other adjusting instruments. Specifically, the optical trial device can be first inserted into the intervertebral space and then adjusted to a desired location using a second instrument. Once the trial device is positioned as desired, the imaging device can be instructed to image the intervertebral space and/or the endplates. The imaging device can be inserted before or after the position of the trial device is adjusted, depending, at least in part, on the configuration of the system and optical trial device and the surgical procedure being performed. In some embodiments, the imaging device can be positioned within the trial device prior to insertion of the device into the surgical site.

Figures 13, 14:
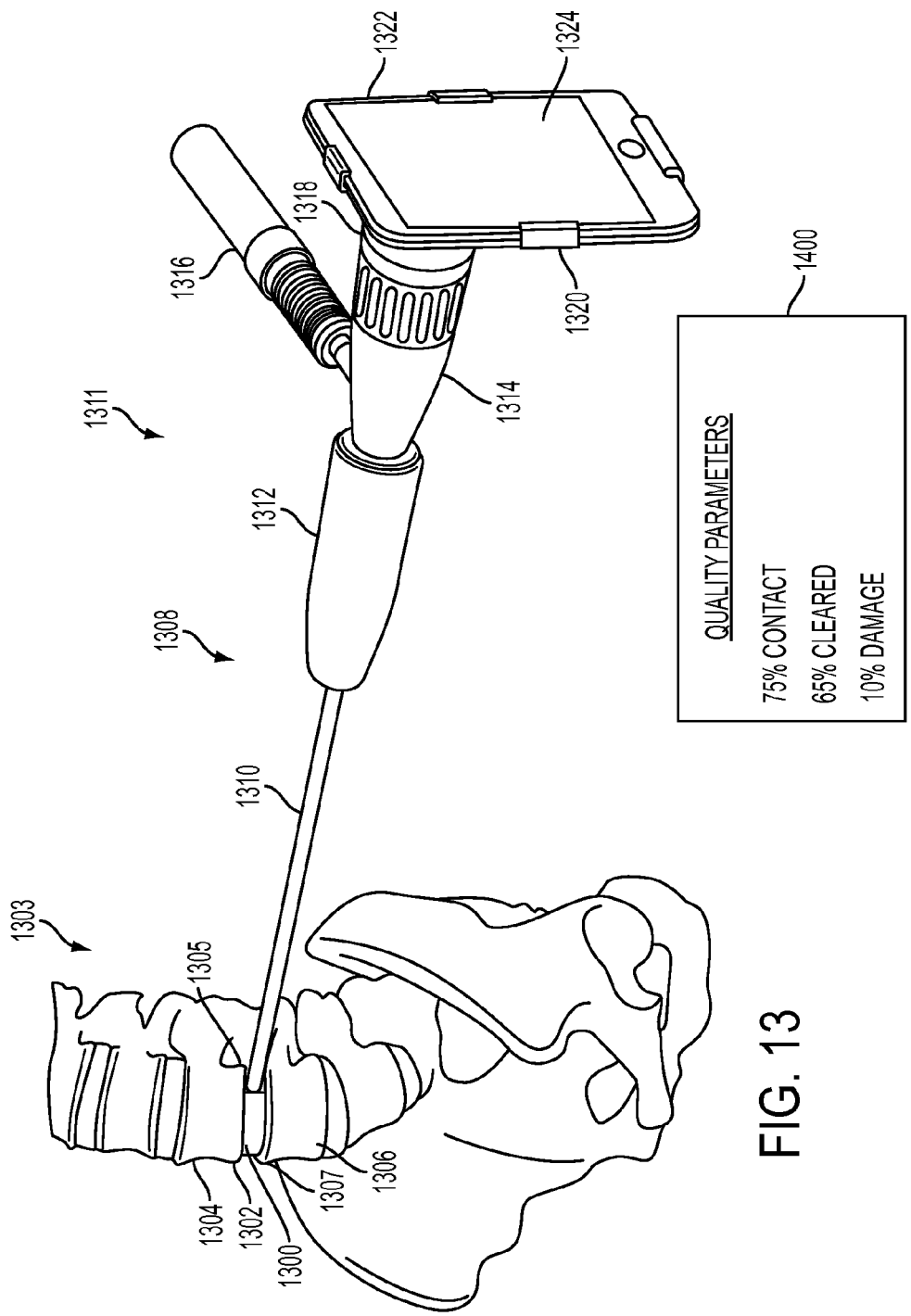
FIG. 13 is a perspective view of a portion of a spinal column with an intervertebral trial device inserted into an intervertebral space, with the intervertebral trial device being coupled, via an eyepiece attachment, with a mobile device, in accordance with some embodiments.
FIG. 14 illustrates exemplary parameters indicating quality of preparation of endplate surfaces for a surgical procedure determined in accordance with some embodiments.

FIG. 13 illustrates an optical trial device 1300 in use. As shown, the device 1300 is inserted into an intervertebral space 1302 between an upper vertebral body 1304 having an endplate 1305 and an adjacent lower vertebral body 1306 having an endplate 1307. FIG. 13 shows only a portion of the patient's spinal column 1303 for simplicity. To prepare the intervertebral space 1302 for a surgical procedure such as a spinal fusion or receipt of an artificial disc implant, a diseased or damaged disc between the adjacent vertebral bodies 1304 and 1306 can be removed. Adequate disc removal and preparation of the surfaces of the endplates 1305 and 1307 may determine the success of the surgical procedure. Accordingly, the optical trial device 1300 can be used to allow the surgeon to visualize the disc space and the endplates to verify the extent and quality of the endplate preparation.

As shown in FIG. 13, the trial device 1300 can be inserted into the intervertebral space 1302 using an instrument 1308 which, in this example, is an endoscope including a shaft 1310 and a base 1312. The endoscope 1308 can be part of an assembly 1311 comprising a light adapter 1314, a light source 1316, an eye piece attachment 1318, and a mobile device attachment 1320. The base 1312 can be connected to the light adapter 1314 coupled with the light source 1316. The light source 1316 can include a light emitting device configured to emit light of a desired wavelength. In some embodiments, the light source can be an ultraviolet light source. Furthermore, in some embodiments, one or more light sources can emit light of different wavelengths.

The light adapter 1314 can be connected to the eye piece attachment 1318 for observing the image transmitted from the imaging device of the optical trial device 1300 to a mobile computing device 1322 associated with the mobile device attachment 1320. The eye piece attachment 1318, mobile device attachment 1320, and mobile computing device 1322 can have similar configurations and capabilities as described elsewhere herein.

As shown in FIG. 13, the mobile device attachment 1320 can seat the mobile computing device 1322 such that a camera of the mobile computing device 1322 is aligned with an opening, or aperture, of the eye piece attachment 1318. Thus, the camera of the mobile computing device 1322 can be used to view and record the information in the field of view of the imaging device (not shown in FIG. 13) positioned within the trial device 1300. Information on the intervertebral space and/or the endplate surface viewed and imaged by the imaging device can be displayed on a screen 1324 of the mobile computing device 1322.

Although not visible in FIG. 13, in this example, the camera of the mobile computing device 1322 is a front-facing camera positioned on a top portion of the mobile computing device 1322. However, it should be appreciated that the mobile computing device 1322 can include one or more cameras located in other portions of the device, in which cases a mobile device attachment having a configuration different from that shown in FIG. 13 can be employed.

The use of the mobile device during the surgical procedure to view the surgical site can be more convenient to the surgeon and other medical personnel because different components are located close to each other and the system is therefore more compact. Accordingly, in contrast to traditional set ups where a surgeon views the surgical site at a display positioned some distance away from the instruments being used to perform the surgery, the described system that does not require the surgeon to look away from the surgical instruments being used to perform the procedure because the display is located in the vicinity of the instruments and the treatment site. The acquired images can be used in real time, or can be stored on a suitable storage media—for example, in a database of patients' records.

Further, because the optical trial device 1300 can be configured to push disc remains, blood and other fluids away from the surgical site, image information of an improved quality can be obtained and displayed on the screen 1324.

Any suitable information can be displayed on the screen 1324. For example, as the imaging device within the trial device 1300 images the intervertebral space 1302 and surface of the endplates 1305 and 1307, these areas can be viewed on the screen 1324. Depending on a light source utilized and any other factors, different types of images can be displayed in different imaging modes. For example, views or images can be acquired of the tissues which are posteriorly-adjacent and/or anteriorly-adjacent to the trial device. In this manner, a visual assessment can be made of the annular release, of the potential graft volume, and/or of conformation of the posterior position of the trial. This information can expand the use of the optical trial into a device that not only assesses endplate preparation but aids in assessing the surgical decompression by confirming the removal of herniated tissue and collapsed ligamentia or the creation of space/voids that relieve nerve compression.

The image information acquired by the imaging device through one or more optically transparent or radiolucent portions of the trial device 1300 can include a single image or multiple images. When a sequence of image frames is acquired, the image frames can then be stitched into a composite image using any suitable image processing technique. In some embodiments, the images can be stored in memory of the mobile computing device 1322 for future use. Additionally or alternatively, the image information can be transmitted from the mobile computing device 1322 to any other computing device. For example, one or more computing devices (e.g., servers) can receive image information from the computing device 1322 and other computing devices similarly coupled with optical trial devices as described herein, and can store such information in association with related patient information (e.g., patient's name, age, medical history, type of surgical procedure performed, etc). The image information can later be reviewed by other medical professionals and can be used for any suitable purposes.

The image information that can be acquired using an optical trial device in accordance with some embodiments can be any suitable information. For example, the image information may comprise an image of the endplates and/or surrounding tissue (e.g., the posterior adjacent tissue, the distally adjacent tissue, etc.). In some embodiments, the image information can be processed in a suitable manner and results of the processing can be displayed on a suitable display, such as a screen of a computing device.

The optical trial device described herein can be used to view the intervertebral space and endplates while being pressed against the endplates. Thus, in some embodiments, imaged areas of the endplates that are contacted by the trial device and areas that are determined to be not in contact with the trial device can be identified. This information can be used in conjunction with the image information to generate a map of the imaged endplate surfaces indicating the contact and non-contact areas. In some embodiments, the map can be similar to an orthotic pressure map. The map of contact and non-contact areas or other similar information may be generated in real time—as the disc space is being imaged through the trial device, and can be displayed in conjunction with the images being captured. Such additional information may help a medical professional during a surgical procedure to make a decision regarding what portion(s) of the disc are not removed or not adequately removed from the endplate surface.

In some embodiments, a computing device, such as the device 1322 or any other computing device, can also be used as a lighting source. Light of varying wavelengths can be used to illuminate the areas being imaged in a suitable manner to aide in capturing clear image information to determine areas of the endplates that have been cleared of cartilage. For example, one or more optical beams of visible, ultraviolet and infrared light can be utilized, and the resulting images of different modalities can be separately or in combination used to evaluate the preparation of the endplate surfaces for the surgical procedure.

In some embodiments, the contact and non-contact areas may be identified and then used to determine qualitative or quantitative parameters indicting the quality of the preparation of the endplate surfaces and the intervertebral space for the surgical procedure. FIG. 14 illustrates an example of information 1400 related to such parameters that can be generated and displayed on a suitable computing device. The information 1400 may include one or more parameters ("Quality Parameters") indicating the extent and quality of preparation of the endplate surfaces for a spinal fusion procedure or receipt of a disc implant.

In FIG. 14, the exemplary parameters include: (a) a percentage of the contact (shown by way of example as "75% contact") to indicate a percentage of the area of the endplate surface that is contacted by the trial device; (b) a percentage of the cleared endplate surface area (shown by way of example as "65% cleared") to indicate a percentage of the surface area that is unencumbered; and (c) a percentage of the damage of the disc (shown by way of example as "10% damage") to indicate an amount of the disc that is damaged. The values of the parameters may be presented in any suitable manner, using any visual and/or audio indicators. For example, different colors and other cues may be used to assist a surgeon in evaluating the preparation of the endplate surfaces. Additionally, this information may be presented on a suitable display or monitor in conjunction with any other useful information—for example, optimal values of one or more of the parameters that are desired to be achieved for a successful outcome of the procedure. Thus, it can be advantageous for medical personnel to view the information in real time to achieve a desired quality of the prepared surgical site.

The values of the quality parameters may be used by the surgeon or other medical professional in any suitable manner. The surgeon may be guided through a disc replacement or spinal fusion procedure using the acquired images of the disc space and the parameters computed based on processing of the images. For example, if a certain percentage of the endplate surface area is required to be cleaned prior to a surgical procedure, the computed percentage of the contact and percentage of the cleared endplate surface area parameters may be used to determine whether the desired percentage of the endplate surface area has been cleared. The computed percentage of the damage of the disc may be used to determine whether the removal of the damaged disc area should continue. This approach can improve a surgeon's experience and facilitate the process of verification of the quality of preparation of the endplate surfaces.

It should be appreciated that quantitative and qualitative values of any suitable parameters indicating the extent and quality of preparation of the endplate surfaces may be computed and displayed to the surgeon, as embodiments are not limited in this respect. For example, other parameters can include identification of any areas of the endplate that are bleeding, a rate of bleeding, blood oxygen levels, and any other determinable information. The information can then be displayed to the surgeon in real time, stored for future use, or utilized in any other suitable manner.

In some embodiments, the information may be utilized by a physician, hospital, or any other health care provider to evaluate techniques and/or various instruments, including newly developed instruments, for disc clearing. In this way, data obtained from multiple providers can be used to determine optimal fusion parameters for spinal fusion procedures. However, it should be appreciated that the described techniques may be used for a variety of purposes, as embodiments are not limited in this respect.

Figure 15:
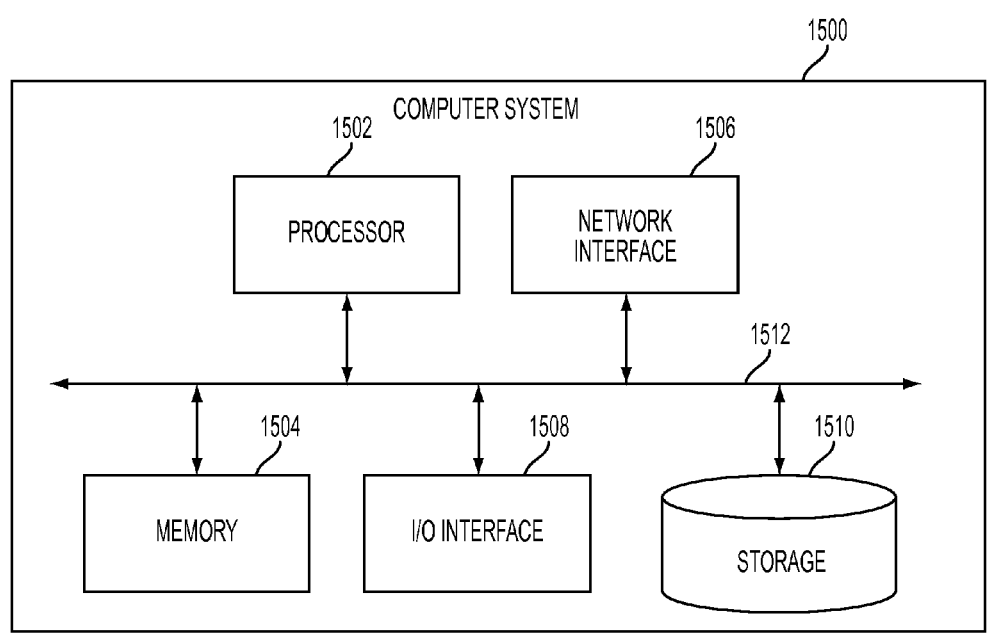
FIG. 15 is a block diagram of an exemplary computing system in which some embodiments can be implemented.

The techniques for processing image information acquired using the optical trial device in accordance with some embodiments can be implemented using any suitable computing system. In some embodiments, image data acquired through the optical trial device may be analyzed and processed by executing, by one or more processors of a computing device, computer-executable instructions stored in at least one tangible, non-transitory computer-readable storage medium of the computing device to determine the areas of contact and non-contact areas and compute any other suitable parameters. When the computer-executable instructions are executed by the one or more processors, the computing device can analyze and process the image data in accordance with some embodiments. For example, computer vision algorithms can be applied to image data captured using the optical trial device to measure or identify anatomic structures within the captured images. By way of further example, structured light techniques can be used to enhance 2D RGB images captured using the optical trial device with depth channel values. These depth channel values can enhance the ability of computer vision algorithms to measure or identify anatomic structures or contours. FIG. 15 illustrates an example of a computing system that may be used in some embodiments.

Computing System

Some of the systems and methods disclosed herein can be implemented using one or more computer systems, such as the exemplary embodiment of a computer system 1500 shown in FIG. 15. As shown, the computer system 1500 can include one or more processors 1502 that can control the operation of the computer system 1500. The processor(s) 1502 can include any type of microprocessor or central processing unit (CPU), including programmable general-purpose or special-purpose microprocessors and/or any one of a variety of proprietary or commercially available single or multi-processor systems. The computer system 1500 can also include one or more memories 1504, which can provide temporary storage for code to be executed by the processor(s) 1502 or for data acquired from one or more users, storage devices, and/or databases. The memory 1504 can include read-only memory (ROM), flash memory, one or more varieties of random access memory (RAM), such as static RAM (SRAM), dynamic RAM (DRAM), or synchronous DRAM (SDRAM), and/or a combination of memory technologies.

The various elements of the computer system 1500 can be coupled to a bus system 1512. The illustrated bus system 1512 is an abstraction that represents any one or more separate physical busses, communication lines/interfaces, and/or multi-drop or point-to-point connections, connected by appropriate bridges, adapters, and/or controllers. The computer system 1500 can also include one or more network interface(s) 1506, one or more input/output (TO) interface(s) 108, and one or more storage device(s) 1510.

The network interface(s) 1506 can enable the computer system 1500 to communicate with remote devices (e.g., other computer systems) over a network, and can be, for example, remote desktop connection interfaces, Ethernet adapters, and/or other local area network (LAN) adapters. The IO interface(s) 1508 can include one or more interface components to connect the computer system 1500 with other electronic equipment. For example, the IO interface(s) 1508 can include high speed data ports, such as USB ports, 1394 ports, etc. Additionally, the computer system 1500 can be accessible to a human user, and thus the IO interface(s) 1508 can include displays, speakers, keyboards, pointing devices, and/or various other video, audio, or alphanumeric interfaces. The storage device(s) 1510 can include any non-transitory computer-readable storage media for storing data in a non-volatile and/or non-transient manner. The storage device(s) 1510 can thus hold data and/or instructions in a persistent state (i.e., the value is retained despite interruption of power to the computer system 1500). The storage device(s) 1510 can include one or more hard disk drives, flash drives, USB drives, optical drives, various media cards, and/or any combination thereof and can be directly connected to the computer system 100 or remotely connected thereto, such as over a network.

The elements illustrated in FIG. 15 can be some or all of the elements of a single physical machine. In addition, not all of the illustrated elements need to be located on or in the same physical or logical machine. Rather, the illustrated elements can be distributed in nature, e.g., using a server farm or cloud-based technology. Exemplary computer systems include conventional desktop computers, workstations, minicomputers, laptop computers, tablet computers, PDAs, mobile phones (e.g., smartphones, etc.), and any other computing devices.

Although an exemplary computer system is depicted and described herein, it will be appreciated that this is for sake of generality and convenience. In other embodiments, the computer system may differ in architecture and operation from that shown and described herein.

Reprocessing

The devices disclosed herein, including but not limited to the optical trial devices, can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., electrodes, a battery or other power source, an externally wearable sensor and/or housing therefore, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

In some embodiments, devices described herein can be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Having thus described several aspects of at least one embodiment, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

For example, in some embodiments, the described optical trial device can be used in connection with a lateral fusion procedure or in a disc replacement procedure. However, it should be appreciated that embodiments are not limited to trial devices used in a specific procedure, and the trial device in accordance with some embodiments can be configured to be used in other intra-discal procedures such as, for example, posterior lumbar interbody fusion (PLIF), transforaminal lumbar interbody fusion (TLIF), anterior lumbar interbody fusion (ALIF), lateral lumbar interbody fusion (XLIF), nucleus and/or annulus replacement or augmentation procedures, or any other procedures. In particular, the trial device can be inserted into the disc space using any of a posterior approach, an anterior approach, a transforaminal approach, a lateral approach, and so forth. Furthermore, it should be appreciated that the described optical trial devices can be used in association with any suitable imaging sensors and light sources, as embodiments are not limited in this respect.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. Aspects described in one embodiment may be combined in any manner with aspects described in other embodiments. For example, one or more of any of the optical trial devices shown in FIGS. 1-11 can be used in combination with the assembly 1200 of FIG. 12 or assembly 1311 of FIG. 13.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The invention claimed is:

1. An intervertebral trial device, comprising:
a trial implant body configured to be placed between adjacent vertebral bodies, the trial implant body having:
an upper trial vertebral end plate surface configured to engage a first vertebral endplate,
a lower trial vertebral endplate surface configured to engage a second vertebral endplate,
a perimeter wall connecting the upper and lower trial vertebral end plate surfaces, the perimeter wall having a distal portion, a proximal portion, and opposed lateral portions,
at least one of the upper trial vertebral end plate surface, the lower trial vertebral end plate surface, and the perimeter wall having at least a portion thereof that is optically transparent or translucent;
an elongated handle extending from a portion of the perimeter wall; and
at least one imaging device;
wherein the elongated handle includes at least one optical fiber coupled with the at least one imaging device, the at least one optical fiber being configured to transmit light from the optically transparent or translucent portion to the at least one imaging device.

2. The intervertebral trial device of claim 1, wherein the trial implant body comprises an optically transparent polymer or crystal.

3. The intervertebral trial device of claim 1, wherein the portion that is optically transparent comprises an opening formed in at least one of the upper trial vertebral end plate surface and the lower trial vertebral end plate surface.

4. The intervertebral trial device of claim 1, wherein the trial implant body is removably and replaceably attached to the elongate handle.

5. The intervertebral trial device of claim 1, wherein a proximal end of the elongated handle is configured to be coupled with an attachment component configured to seat a computing device.

6. The intervertebral trial device of claim 1, wherein the portion that is optically transparent comprises at least one lens or prism.

7. The intervertebral trial device of claim 6, wherein the at least one lens or prism is removably disposed at least partially within the body.

8. The intervertebral trial device of claim 1, wherein the portion that is optically transparent comprises at least one opening formed in the perimeter wall.

9. The intervertebral trial device of claim 8, wherein the at least one opening is formed in the distal portion of the perimeter wall.

10. The intervertebral trial device of claim 1, wherein the portion that is optically transparent has at least one optical component for acquiring images of at least one of an intervertebral space between the adjacent vertebral bodies and at least one of the first and second vertebral endplates.

11. The intervertebral trial device of claim 1, wherein the trial implant body is expandable.

12. A method of verifying preparation of adjacent vertebral bodies for receiving an implant, comprising:
preparing an endplate surface of at least one of the adjacent vertebral bodies for a surgical procedure;
positioning an optical trial device into an intervertebral space between the adjacent vertebral bodies; and
verifying preparation of the endplate surface for receipt of an implant or a spinal fusion procedure by viewing portions of the intervertebral space and the endplate surface through the optical trial device positioned into the intervertebral space,
wherein the optical trial device comprises a trial implant body that is formed entirely of an optically transparent polymer or crystal.

13. The method of claim 12, wherein verifying preparation of the endplate surface comprises acquiring at least one image of at least one of an intervertebral space between the adjacent vertebral bodies and the endplate surface.

14. A method of verifying preparation of adjacent vertebral bodies for receiving an implant, comprising:
preparing an endplate surface of at least one of the adjacent vertebral bodies for a surgical procedure;
positioning an optical trial device into an intervertebral space between the adjacent vertebral bodies; and
verifying preparation of the endplate surface for receipt of an implant or a spinal fusion procedure by viewing portions of the intervertebral space and the endplate surface through the optical trial device positioned into the intervertebral space, wherein the optical trial device comprises an expandable trial device, and the method further comprises inflating the expandable trial device when the expandable trial device is positioned in the intervertebral space.

15. An intervertebral trial kit, comprising:

a plurality of optical trial devices, each configured to be placed in a prepared disc space between adjacent vertebral bodies and having:
  an optical trial implant body configured to be placed between adjacent vertebral bodies, the optical trial implant body having:
  an upper trial vertebral endplate surface configured to engage a first vertebral endplate,
  a lower trial vertebral endplate surface configured to engage a second vertebral endplate, and
  a perimeter wall connecting the upper and lower trial vertebral endplate surfaces, the perimeter wall having a distal portion, a proximal portion, and opposed lateral portions, wherein at least one of the upper trial vertebral endplate surface, the lower trial vertebral endplate surface, and the perimeter wall has at least one portion thereof that is optically transparent, and the kit further comprising:

an attachment component configured to seat a computing device that is configured to receive images of at least one of an intervertebral space between the adjacent vertebral bodies and at least one endplate of the adjacent vertebral bodies through the at least one portion that is optically transparent.

16. The intervertebral trial kit of claim 15, further comprising:
  an elongated handle configured to be removably attached to a portion of an optical trial device of the plurality of optical trial devices.

17. An intervertebral trial device, comprising:
  a trial implant body configured to be placed between adjacent vertebral bodies, the trial implant body having:
  an upper trial vertebral endplate surface configured to engage a first vertebral endplate,
  a lower trial vertebral endplate surface configured to engage a second vertebral endplate,
  a perimeter wall connecting the upper and lower trial vertebral endplate surfaces, the perimeter wall having a distal portion, a proximal portion, and opposed lateral portions,
  at least one of the upper trial vertebral endplate surface, the lower trial vertebral endplate surface, and the perimeter wall having at least a portion thereof that is optically transparent or translucent;
  an elongated handle extending from a portion of the perimeter wall; and
  at least one imaging device,
  wherein a proximal end of the elongated handle is configured to be coupled with an attachment component configured to seat a computing device.

* * * * *